United States Patent [19]

Lanfranconi et al.

[11] Patent Number: 5,383,579
[45] Date of Patent: Jan. 24, 1995

[54] CONTAINER FOR CONTAINING TWO FLOWABLE MATERIALS IN SEPARATED COMPARTMENTS, BUT PERMITTING THE TWO MATERIALS TO BE MIXED FOR DISPENSING, BEFORE THE CONTAINER IS OPENED

[75] Inventors: Antonio Lanfranconi; Giorgio Munari, both of Milan, Italy

[73] Assignee: Inge, S.p.A., Milan, Italy

[21] Appl. No.: 957,186

[22] Filed: Oct. 7, 1992

[30] Foreign Application Priority Data

Oct. 7, 1991 [IT] Italy ............................ MI91A002656

[51] Int. Cl.⁶ ................................................ B67B 5/56
[52] U.S. Cl. ...................................... 222/129; 604/89; 604/416
[58] Field of Search ...................... 604/37, 110, 87–91, 604/416; 222/129, 541, 215

[56] References Cited

U.S. PATENT DOCUMENTS

| | | | |
|---|---|---|---|
| 3,163,163 | 12/1964 | Wilburn | 128/272 |
| 3,354,883 | 11/1967 | Southerland | 222/215 |
| 3,674,028 | 7/1972 | Ogle | 128/272 |
| 4,193,698 | 3/1980 | Gartner | 366/130 |
| 4,405,306 | 9/1983 | Pritchard et al. | 604/87 |
| 4,709,705 | 12/1987 | Truglio | 604/37 |
| 4,982,875 | 1/1991 | Pozzi et al. | 604/87 |
| 5,195,966 | 3/1993 | Corby | 604/88 |

FOREIGN PATENT DOCUMENTS 0395758 11/1990 European Pat. Off. .

*Primary Examiner*—Jerome L. Kruter
*Attorney, Agent, or Firm*—Cushman Darby & Cushman

[57] ABSTRACT

A device for containing and dispensing a flowable material, for once-only use includes a container, to the delivery mouth of which a cannula can be fitted. The container includes a body and a sealed chamber which are separated by a stopper, which is neutralizable by bending or compressing a deformable portion of the body relative to the sealed chamber.

7 Claims, 4 Drawing Sheets

CONTAINER FOR CONTAINING TWO FLOWABLE MATERIALS IN SEPARATED COMPARTMENTS, BUT PERMITTING THE TWO MATERIALS TO BE MIXED FOR DISPENSING, BEFORE THE CONTAINER IS OPENED

BACKGROUND OF THE INVENTION

This invention relates to a device for once-only use, preferably for application to hygiene.

In the field of the aforementioned devices and in particular those used for administering vaginal washes or enemas, devices for once-only use are known comprising a deformable container, to the mouth of which a cannula can be sealedly fixed for insertion into the patient's body.

Known devices for once-only use are sold with the container already filled with the solution ready for use and with their mouth sealed by a stopper which is removable, preferably manually. For hygienic reasons the cannula is packaged separately in a sealed packet, but sold together with the container.

The user (after necessarily shaking the container to revive the solution) removes the stopper from the mouth, withdraws the cannula from its package and fits it to the container mouth to obtain a device ready for use.

The container of such devices is made of plastics material, as it has necessarily to be impermeable, soft and flexible.

Experience has, however, shown that plastics material is not the best material for preserving certain substances which, being ready for use, are particularly active and hence aggressive and/or instable, and consequently of limited life.

To overcome this drawback, devices have been considered comprising two containers of different capacity, plus the already known cannula. One container is filled with some of the components of the solution and the other is filled with the remaining components. The division is obviously made so as to reduce the chemical activity of the components to a minimum, so achieving low aggressivity, substantial chemical stability and a long life. Such devices can therefore be constructed of plastics material at low cost.

Forming the device as two containers can also be dictated by other requirements known to the expert but not mentioned herein for brevity.

To form the solution ready for use the user has to pour the contents of the smaller container into the larger container in addition to carrying out all the operations already mentioned in relation to the preceding case, i.e., removing the stopper from two containers and fitting the cannula. There is also an obvious danger in pouring substances which usually have a high capacity for impregnation and hence a high staining power.

In addition, this type of device does not allow optimum mixing of the contents of the two containers if the contents are poorly miscible with each other. In such a case, the solution ready for use can only be achieved in an open container closable by the user's fingers during shaking, with the possibility both of contaminating the product and producing accidental splashing.

Hence, in the current state of the art, the devices in use may comprise one or two containers. The choice is obviously dictated by the type of solution to be sold.

SUMMARY OF THE INVENTION

The object of the present invention is to provide a device by which the above-mentioned drawbacks are obviated, i.e., a device for once-only use preferably for application to hygiene, which allows relatively long-term preservation of tendentially unstable solutions aggressive towards the materials of construction of the device (preferably plastics material), even if the solutions comprise components which are difficult to mix and which hence generally require strong shaking of the solution before use, but without the user having to resort to uncomfortable pouring.

By compressing the sealed chamber and bending it relative to the container body, the stopper means are neutralized by virtue of their at least partial removal, to hence connect the container body to the sealed chamber, allowing consequent mixing of the two products without the container mouth having to be unsealed. The neutralization of the stopper means can be achieved either by breaking it along a preferential line on the stopper or by removing the stopper from its seat. Because the device itself is still sealed, the solution can be energetically shaken before use with total safety. In addition, by correctly dividing the components of the solution to be obtained by mixing, the chemical activity of the components can be reduced to a minimum, to the benefit of the preservability and integrity of the device materials.

BRIEF DESCRIPTION OF THE DRAWINGS

The invention is illustrated by way of a non-limiting example which is shown in the figures of the accompanying drawings.

In the drawings.

DETAILED DESCRIPTION

Figure 1:
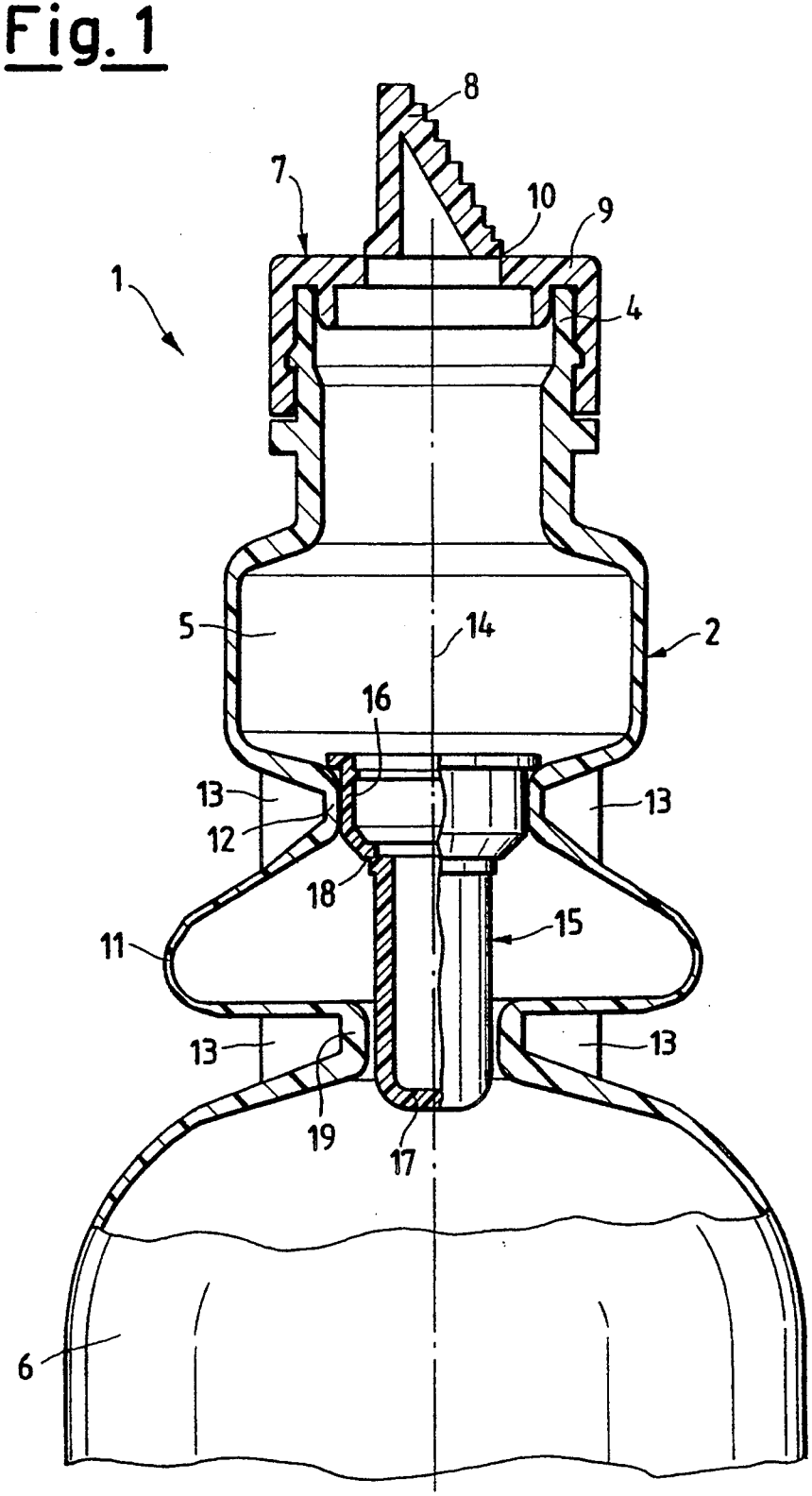
FIG. 1 is a fragmentary partial longitudinal section through a device according to an embodiment of the invention of the type intended for containing and dispensing example for vaginal washes.
Figure 2:
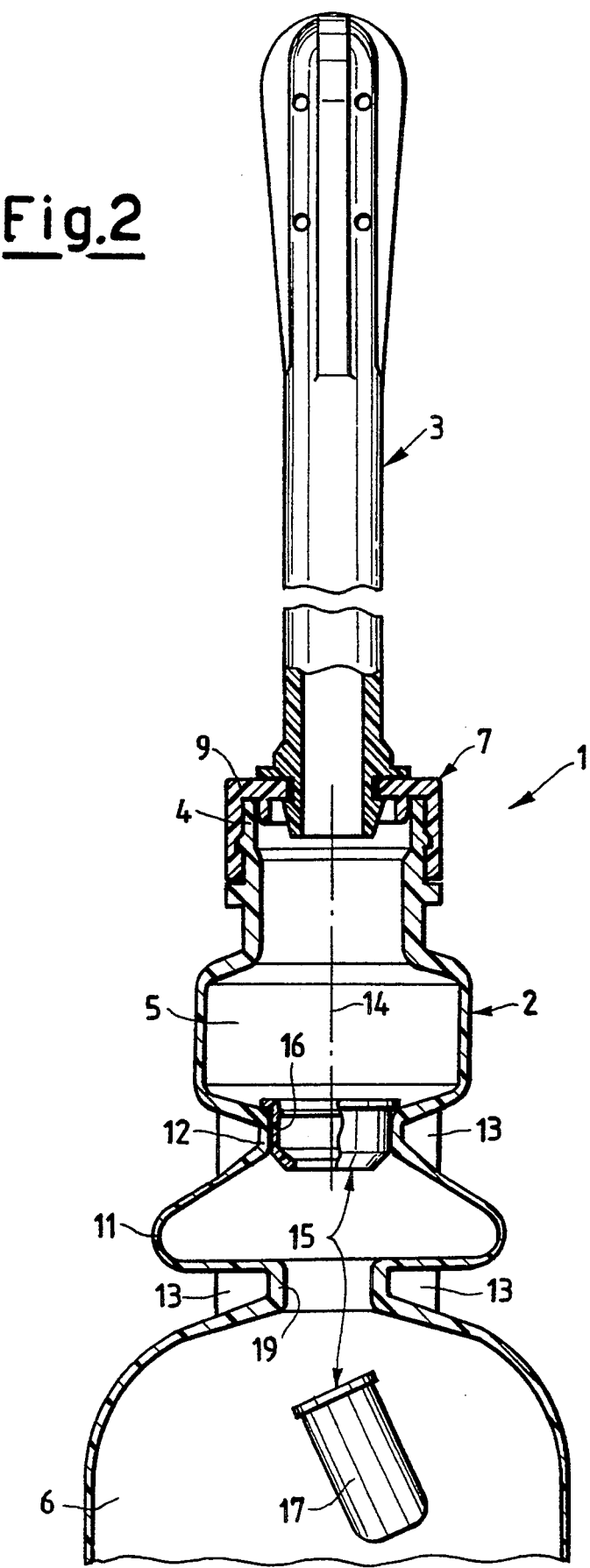
FIG. 2 is a similar section through the device of FIG. 1 when made ready for use.

With reference to FIGS. 1 and 2, the device of the first embodiment of the invention, indicated overall by 1, comprises a container 2 and a cannula 3.

The container 2 comprises a delivery mouth 4, a sealed chamber 5 and a body 6. The delivery mouth 4 is sealed by a manually removable cap 7.

To facilitate sealing and removal the cap 7 comprises an appendix 8 acting as a guarantee seal, which when bent separates from the remaining part 9 of the cap along a preferential fracture edge 10.

The sealed chamber 5 is positioned between the delivery mouth 4 and the deformable body 6. The sealed chamber 5 comprises a mouth 12 connecting to the body 6 of the container 2 and sealed by neutralizable stopper means, which vary according to the type of device.

In proximity to the connection mouth 12 the container body 6 comprises a deformable portion 11 preferably of bellows structure provided at its two ends with opposing pairs of ribs 13.

The thickness and structure of the portion 11 are such that it is much more flexible than the surrounding structures, both when stressed in a direction parallel and when stressed in a direction perpendicular to the delivery axis 14. The neutralizable stopper means can be one of at least two types, each of which is at least partly removable.

A first type of the neutralizable stopper means, the one which is shown in FIGS. 1 and 2, comprises a hollow body 15 formed from a portion of open trapezoidal section 16 continuously joined to a closed (very slightly) conical and, therefore, seemingly cylindrical portion 17 along a preferential fracture line 18. After the deformable body 6 has been filled, the hollow body 15 is pressed into the connection mouth 12. More specifically, the open trapezoidal portion 16 is pressed into the mouth 12, as a result of which the closed slightly conical, generally cylindrical portion 17 is slackly inserted into an annular restriction 19.

Neutralization of this first type of stopper means is achieved by simply pressing the sealed chamber 5 and then bending it relative to the body 6 along the axis 14.

However, the stopper means can also be neutralized by merely bending the sealed chamber 5 relative to the body 6 along the axis 14. In this case the closed slightly conical, generally cylindrical portion 17 is preferably of greater length than shown in FIG. 1.

The annular restriction 19 thus presses against the side of the closed slightly conical, generally cylindrical portion 17 while the connection mouth 12 locks the open trapezoidal portion 16. The hollow body 15 is hence bent and breaks along the preferential fracture line 18, the closed slightly conical, generally cylindrical portion 17 then separating from the portion 16 of trapezoidal section, to fall into the body 6.

Although remaining in position in the mouth 12 the open trapezoidal portion 16 is no longer closed, and connects the container 6 to the sealed chamber 5, to allow the two products to be mixed together.

Figure 3:
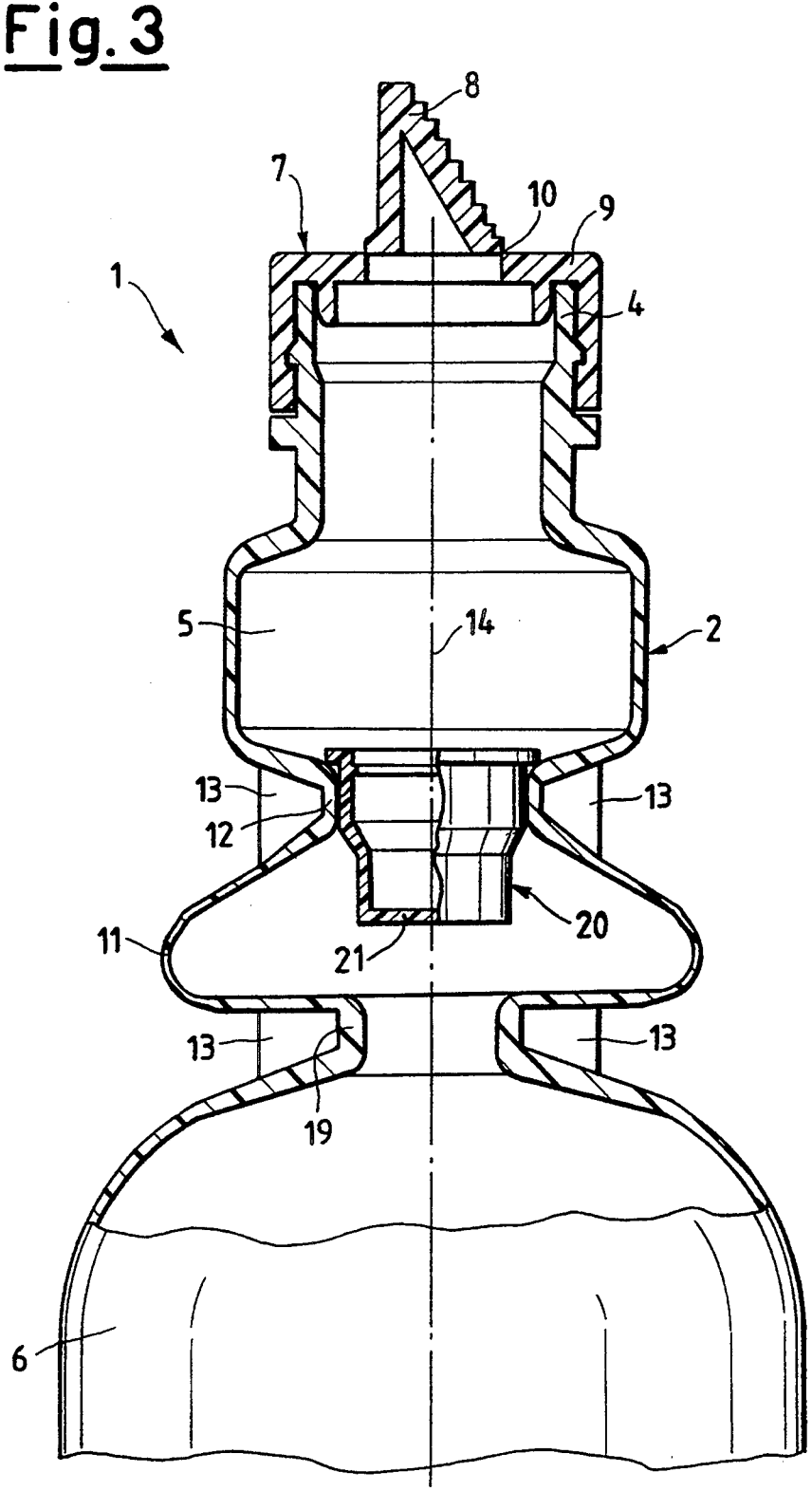
FIG. 3 is a fragmentary partial longitudinal section through a further embodiment of a device according to the invention.
Figure 4:
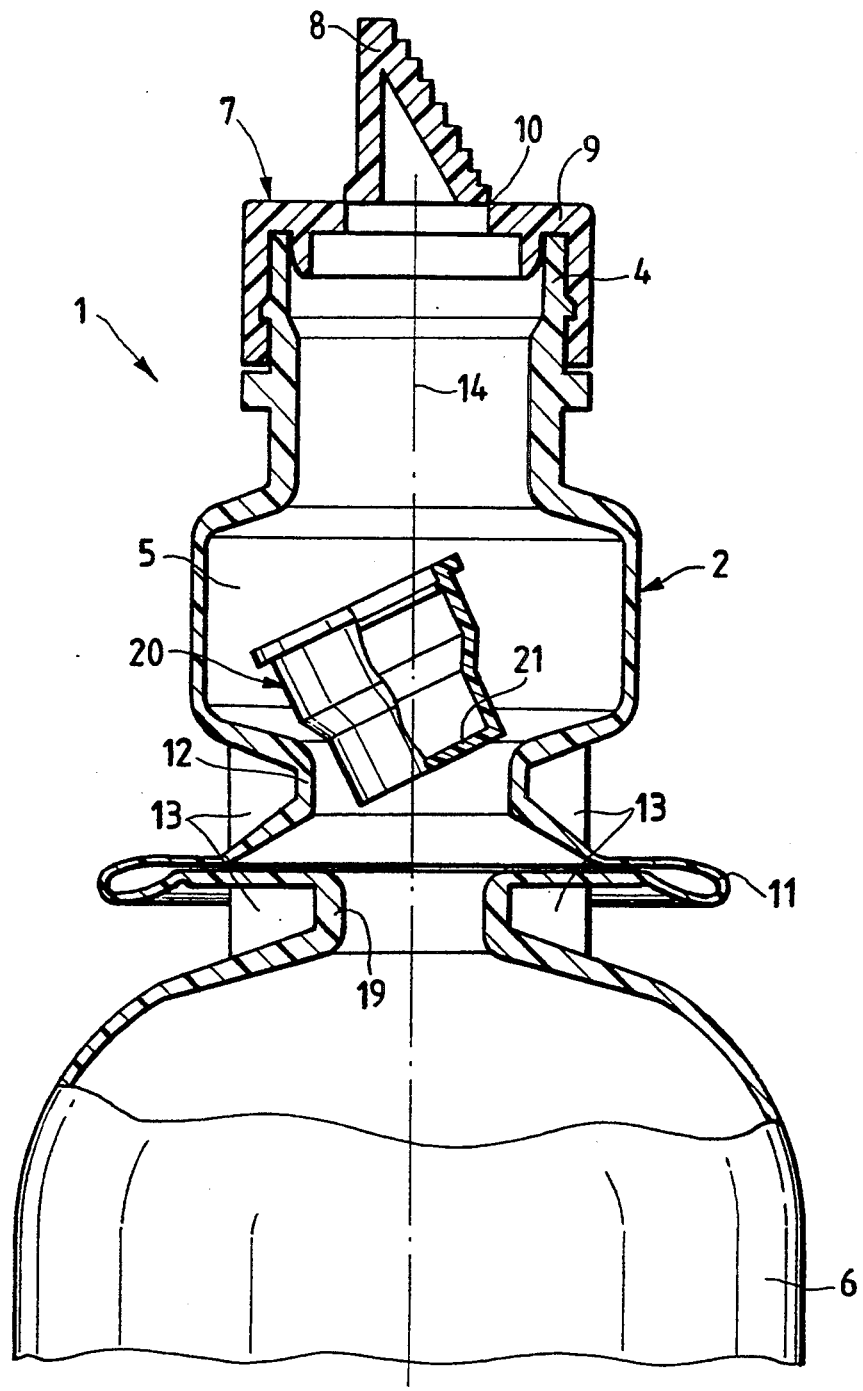
FIG. 4 is a similar section through the device of FIG. 3, but shown during the removal of the stopper in order to ready the device for use.

The second type of neutralizable stopper means, shown in FIGS. 3 and 4, comprises only a closed portion 20 of trapezoidal section. After the deformable body 6 has been filled, the closed trapezoidal portion 20 is pressed into the connection mouth 12 to form the seal.

Neutralization of this second type of stopper means is achieved by simply pressing the sealed chamber 5 against the body 6 along the axis 14. As the portion of closed trapezoidal section 20 (or rather its base wall 21 perpendicular to the axis 14) is of greater diameter then the annular restriction 19, it presses frontally against the inner walls of the restriction 19 and is pushed out of the mouth 12. In this case the removal of the stopper means is total. The two above described stopper means are interchangeable, so that when assembling the device 1 one type can replace the other and vice versa on the container 6.

In both cases the stopper means are removed while the container is still hermetically sealed by the manually removable appendix 8. Hence the container can be energetically shaken without any danger of the solution escaping. Hence poorly miscible solution components can also be adequately mixed together. In addition, if the solution is particularly aggressive it can be preserved until use separated in one and the same container into components of reduced chemical aggressivity and consequently for a long period without any solution alteration and/or container perforation occurring.

After shaking, the user presses on the appendix 8 so that it bends relative to the axis 14, and is removed to leave a free opening. One end of the cannula 3 can then be pushed in at the preferential fracture edge 10 which forms, to hence make the device ready for use. The cannula 3 can be replaced by any other type of delivery member if required.

The device 1 can also be used in sectors other than the hygiene sector, and generally in all those sectors in which unstable and/or particularly corrosive solutions are sold ready for use, even if the individual components of the solutions are miscible only by energetic shaking. In addition, the compactness of the device (which comprises only one container) allows better use of the available space when packaging the device.

We claim:

1. A container for containing two flowable materials in separated compartments, but permitting the two materials to be mixed for dispensing, before the container is opened, said container comprising:

peripheral sidewall means defining a first chamber for containing a first flowable material, said sidewall means having two axially opposite ends;

means defining an annular mouth at one said end of said peripheral sidewall means;

a deformable body defining a second chamber for containing a second flowable material, said deformable body being closed at one end and having means defining an annular restriction at an axially opposite end thereof;

said first and second chambers being arranged with one end of said peripheral sidewall means disposed adjacent but axially spaced from said opposite end of said body along a longitudinal axis of said container;

a tubular, annularly corrugated bellows axially joining said mouth with said annular restriction; said bellows being more easily deformable than are said peripheral sidewall means and said body adjacent said bellows;

an openable closure cap closing the opposite said end of said peripheral sidewall means;

a stopper seated in said mouth and thereby interruptably sealing said first chamber from said second chamber; said stopper including a structural feature which is engageable with said annular restriction upon flexing of said bellows, despite said closure cap remaining in closing relation to said opposite end of said peripheral sidewall means, for effectively disrupting said stopper and thereby effectively interconnecting said first chamber with said second chamber through said annular restriction, said bellows and said mouth, whereby flowable materials in said first and second chambers can be mixed by shaking said container after disrupting said stopper.

2. The container of claim 1, wherein:

said closure cap includes an appendix frangibly connected to a main portion thereof along a fracturing edge, which, when fractured, provides an opening; and a dispenser having a fitting for mounting said dispenser in said opening for permitting mixed flowable material to be dispensed from said container therethrough.

3. The container of claim 2, wherein:
said dispenser is an elongated cannula.
4. The container of claim 1, wherein:
said structural feature is arranged to cause said stopper to be bodily dislodged from sealing relation to said mouth upon engagement of said structural feature with said annular restriction.
5. The container of claim 1, wherein:
said stopper is a thimble-shaped structure having an end wall and a peripheral sidewall; said sidewall of said stopper being provided with a circumferentially extending line of weakness; and said structural feature is arranged to cause said stopper to separate into two pieces and axially separate along said line of weakness upon engagement of said structural feature with said annular restriction.
6. The container of claim 1, wherein:
said structural feature is arranged to participate in said engagement upon axial condensing of said bellows.
7. The container of claim 1, wherein:
said structural feature is arranged to participate in said engagement upon bowing of said bellows in a sense to bend said container on said axis.

* * * * *